United States Patent [19]
Chino et al.

[11] Patent Number: 5,435,171
[45] Date of Patent: Jul. 25, 1995

[54] APPARATUS FOR AUTOMATICALLY PREPARING SOLUTION OF POWDERY PRODUCT AS SPECIMEN FOR USE IN VISCOSITY MEASUREMENT

[75] Inventors: Takashi Chino, Iruma; Yuji Nogami, Kawaguchi; Hajime Yashiro, Sagara; Keisuke Kato, Kawasaki; Hajime Kitamura, Ichihara; Masaru Takeuchi; Hideo Yoshikoshi, both of Hasaki; Mikio Kitai, Mito, all of Japan

[73] Assignee: Shin-Etsu Chemical Co., Ltd., Japan

[21] Appl. No.: 171,734

[22] Filed: Dec. 22, 1993

[30] Foreign Application Priority Data

Jan. 4, 1993 [JP] Japan .................................. 5-000095

[51] Int. Cl.⁶ ...................... G01N 35/00; G01N 1/28; B01J 4/02
[52] U.S. Cl. ................ 73/64.56; 73/863.01; 73/1 R; 436/19; 436/8
[58] Field of Search ................ 73/64.56, 863.01, 1 R, 73/53.01, 53.04, 54.11, 61.41, 61.43, 54.07; 436/8, 19

[56] References Cited

U.S. PATENT DOCUMENTS 4,794,806  1/1989  Nicoli et al. .................. 73/863.01

FOREIGN PATENT DOCUMENTS 2-14731  1/1990  Japan .......................... 436/8

Primary Examiner—Hezron E. Williams
Assistant Examiner—J. David Wiggins
Attorney, Agent, or Firm—Parkhurst, Wendel & Rossi

[57] ABSTRACT

An apparatus for supplying a solution of a powdery product as a specimen of viscosity measurement. The apparatus includes electronic discharge-weighing device (4) for determining the amount of the powdery sample in sample container (2), introduced into hopper (6) and discharged therefrom by vibration-generating drive (5); dissolution container (12) for receiving and dissolving the powdery sample from hopper (6); electronic balance (13) for weighing the powdery sample in container (12); supply source (14) for solvent into container (12); device (36) for heating and stirring the powdery sample and the solvent in container (12), and a control circuit for controlling the apparatus.

14 Claims, 5 Drawing Sheets

APPARATUS FOR AUTOMATICALLY PREPARING SOLUTION OF POWDERY PRODUCT AS SPECIMEN FOR USE IN VISCOSITY MEASUREMENT

BACKGROUND OF THE INVENTION

The present invention relates to an apparatus for automatically dissolving a powdery resin product such as a vinyl chloride resin, an ABS resin or an MBS resin in a solvent to give a solution having a predetermined concentration for use in viscosity measurement.

When preparing resin powder or forwarding the powdery product from a manufacturing plant, the powdery product is in general subjected to quality inspection for confirming whether the product fulfills the requirements for various predetermined properties. The results thus obtained are sent back to the manufacturing plant for the improvement of production processes or they are used in the denoration of the quality in order to afford convenience to the destination or the consignee.

In case of, for instance, vinyl chloride resin powder, one of the items for quality inspection thereof is to determine the average degree of polymerization. The determination of the average degree of polymerization of a powdery resin product has currently been carried out, as specified in JIS-K-6721, by determining viscosities of solutions of a resin product having a series of proper concentrations to obtain the intrinsic viscosity thereof and then evaluating the average degree of polymerization on the basis of the resulting intrinsic viscosity. Examples of devices for the determination of such an intrinsic viscosity include an automatic viscosity-determining device available from Rigo Co., Ltd. under the trade name of VSM-052PC.F01.

The viscosity measurement by an automatic viscosity-determining apparatus requires the preparation of a series of solutions of a powdery resin sample each having a predetermined concentration. There has not conventionally been developed any apparatus for preparing such a solution by automatically dissolving a powdery resin sample in a solvent. The preparation of a solution of a powdery resin sample for use in the viscosity determination thereof requires not only accurate weighing of a powdery resin sample, but also accurate weighing of a solvent. In the conventional methods, however, such operations for the preparation of solutions used in the automatic viscosity-determination have been manually performed. Accordingly, the preparation of this type requires much labor and time and is inefficient. Moreover, operations for preparing such a solution slightly vary depending on the operators and this is reflected in the resulting measured values.

SUMMARY OF THE INVENTION

The present invention has been developed for the solution of the foregoing problems associated with the conventional techniques and accordingly, an object of the present invention is to provide an apparatus for automatically preparing a solution of a powdery product as a specimen for use in a viscosity-determination, which is an apparatus for preparing a solution (or specimen) of a powdery sample and supplying the solution to a viscosity-determining device (viscometer) and in which the powdery product is automatically dissolved in a solvent to give a specimen having a predetermined concentration.

According to the present invention, there is provided an apparatus for preparing a solution of a powdery product having a predetermined concentration as a specimen for use in a viscosity measurement which comprises an electronic discharge-weighing device for determining the discharged amount of a powdery sample which is accommodated in a sample container, introduced into a hopper and discharged from the hopper by the operation of a drive unit for generating vibration; a container for receiving and dissolving the powdery sample discharged from the hopper; an electronic balance for weighing the powdery sample in the dissolution container; a solvent supply source for injecting a solvent into the dissolution container containing the powdery sample; a device for heating and stirring the powdery sample and the solvent in the dissolution container; and a control circuit which is connected to the electronic discharge-weighing device, the drive unit for generating vibration, the electronic balance, the solvent source and the heating and stirring device, whereby the control circuit activates the vibration-generating drive unit in proportion to the discharged amount of the powdery sample detected by the electronic discharge-weighing device and it also activates the solvent supply source in proportion to the required amount of the solvent which is calculated by the control circuit on the basis of the amount of the powdery sample weighed by the electronic balance and inputted to and stored in the control circuit.

DESCRIPTION OF THE PREFERRED EMBODIMENTS

The apparatus for automatically preparing a solution of a powdery product as a specimen for use in viscosity-determination according to the present invention which has been developed for the solution of the foregoing problems will hereunder be described in more detail with reference to the accompanying FIGS. 1 and 3 which correspond to embodiments of the apparatus of the present invention.

The apparatus of the present invention is designed to prepare a solution of a powdery product having a predetermined concentration as a specimen for use in the viscosity-determination thereof. As seen from FIG. 1, the apparatus comprises electronic discharge-weighing device 4 for determining the discharged amount of a powdery sample which is accommodated in sample container 2, introduced into hopper 6 and discharged from hopper 6 by the vibrational action of drive unit 5 for generating vibration; dissolution container 12 for receiving and dissolving the powdery sample discharged from hopper 6; electronic balance 13 for weighing the powdery sample in dissolution container 12; solvent supply source 14 for injecting a solvent into dissolution container 12 containing the powdery sample; and device 36 for heating and stirring the powdery sample and the solvent present in dissolution container 12. As seen from FIG. 3, the apparatus further comprises control circuits 61, 62 and 63 which are connected to electronic discharge-weighing device 4, vibration-generating drive unit 5, electronic balance 13, solvent supply source 14 and heating and stirring device 36, whereby control circuit 63 activates vibration-generating drive unit 5 in proportion to the discharged amount of the powdery sample detected by electronic discharge-weighing device 4 and control circuits 61 and 62 activate solvent supply source 14 in proportion to the required amount of the solvent which is calculated by control circuits 61 and 62 on the basis of the amount of the powdery sample weighed by electronic balance 13.

Preferably, this apparatus is also provided with robot 3 for holding and transporting sample container 2 and dissolution container 12, and robot 3 is put in operation under the control of control circuits 61 and 62. Moreover, viscosity-determining device 35 is preferably arranged within the region in which robot 3 can move or perform its operations.

Figure 2:
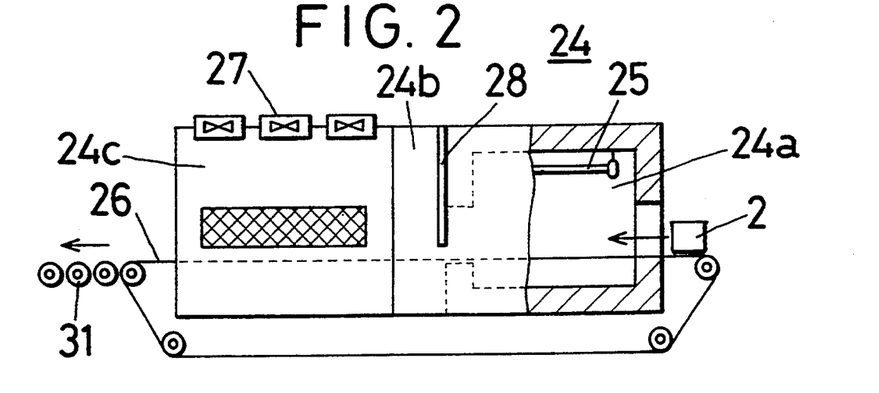
FIG. 2 is a cross-sectional view showing a tunnel furnace attached to the apparatus for automatically preparing a solution of a powdery product as a specimen for use in viscosity-determination according to the present invention.

As seen from FIG. 2, the apparatus of the present invention is further provided with, on the side from which the powdery sample is supplied, tunnel furnace 24 provided with conveyor 26 which comprises heating-drying zone 24a in which hot air heated by infrared heater 25 is circulated; buffer zone 24b for maintaining the temperature in heating-drying zone 24a at a predetermined level; and ordinary temperature zone 24c in which outside air is circulated. Thus sample container 2 accommodating a powdery sample is preferably introduced into tunnel furnace 24 by the action of conveyor 26 to heat and dry the powdery sample and then introduced into hopper 6.

Discharge chute 7 connected to the lower opening of hopper 6 is inclined to such an extent that any powdery sample does not cause free flow, but flow down by the vibrational force applied thereto through vibration-generating drive unit 5 and vibration-generating drive unit 5 is put in operation by the control signal inputted thereto through control circuit 63 on the basis of the weighed value inputted to the circuit through electronic discharge-weighing device 4. Thus, the amount of the powdery sample discharged from hopper 6 can be adjusted so that it is in conformity with the value previously inputted to and stored in control circuit 63.

Hopper 6 connected to vibration-generating drive unit 5 is preferably mounted on electronic dicharge-weighing device 4 through shock absorber 8.

The apparatus further comprises suction port 11 which is communicated to suction drive unit 10 and suction port 11 can move up and down to the position in close proximity to the bottoms of the hopper and discharge chute 7 in response to the action of drive unit 15 for moving suction port 11 up and down. Preferably, suction port 11 is formed into box-like body 16 having a shape approximately similar to those of hopper 6 and discharge chute 7, and suction port 11 is positioned so as to maintain very short and constant distances between port 11 and the side wall and bottom of hopper 6 and between port 11 and the bottom of discharge chute 7. The very short and constant distances specifically range from 0.5 to 5 mm, respectively. Preferably, the ascending and/or descending speed of suction port 11 can be adjusted to not more than 40 cm/sec by the control through drive unit 15 for moving port 11 up and down.

In the present invention, the apparatus for automatically preparing a solution of a powdery product as a specimen for use in viscosity-determination can be applied to powdery samples such as vinyl chloride resin powder.

The powdery sample accommodated in sample container 2, which is introduced into hopper 6, is discharged from the hopper through the application of vibrational force generated by vibration-generating drive unit 5. At this stage, electronic discharge-weighing device 4 operates to determine the weight reduction of the powdery sample contained in the hopper, i.e., the amount of the powdery sample discharged from the hopper and inputs the values thus determined to control circuit 63. The amount of the powdery sample required for the preparation of a solution thereof having a predetermined concentration has previously been inputted and stored in control circuit 61 and the set values has been forwarded to control circuit 63. Vibration-generating drive unit 5 is interrupted through the control by control circuit 63 at an instance when the amount of the powdery sample weighed by electronic discharge-weighing device 4 reaches the set value, in order to terminate the discharge of the powdery sample from the hopper. The predetermined amount of the powdery sample which is discharged from the hopper is received by dissolution container 12 and weighed by electronic balance 13. Control circuit 61 calculates the amount of a solvent required for the preparation of the solution of the powdery resin sample having a predetermined concentration on the basis of the weight of the sample thus determined. Solvent supply source 14 is put in operation under the control of control circuit 61 and the solvent is injected into dissolution container 12. Dissolution container 12 containing the required amounts of the powdery sample and the solvent is transferred to heating-stirring device 36 wherein the powdery sample is dissolved in the solvent to give a desired solution and the resulting solution is used for the viscosity-determination in viscosity-determining device 35.

Specific embodiments of the present invention will hereunder be described in more detail with reference to the accompanying drawings, but the present invention is by no means limited to these specific embodiments.

Figure 1:
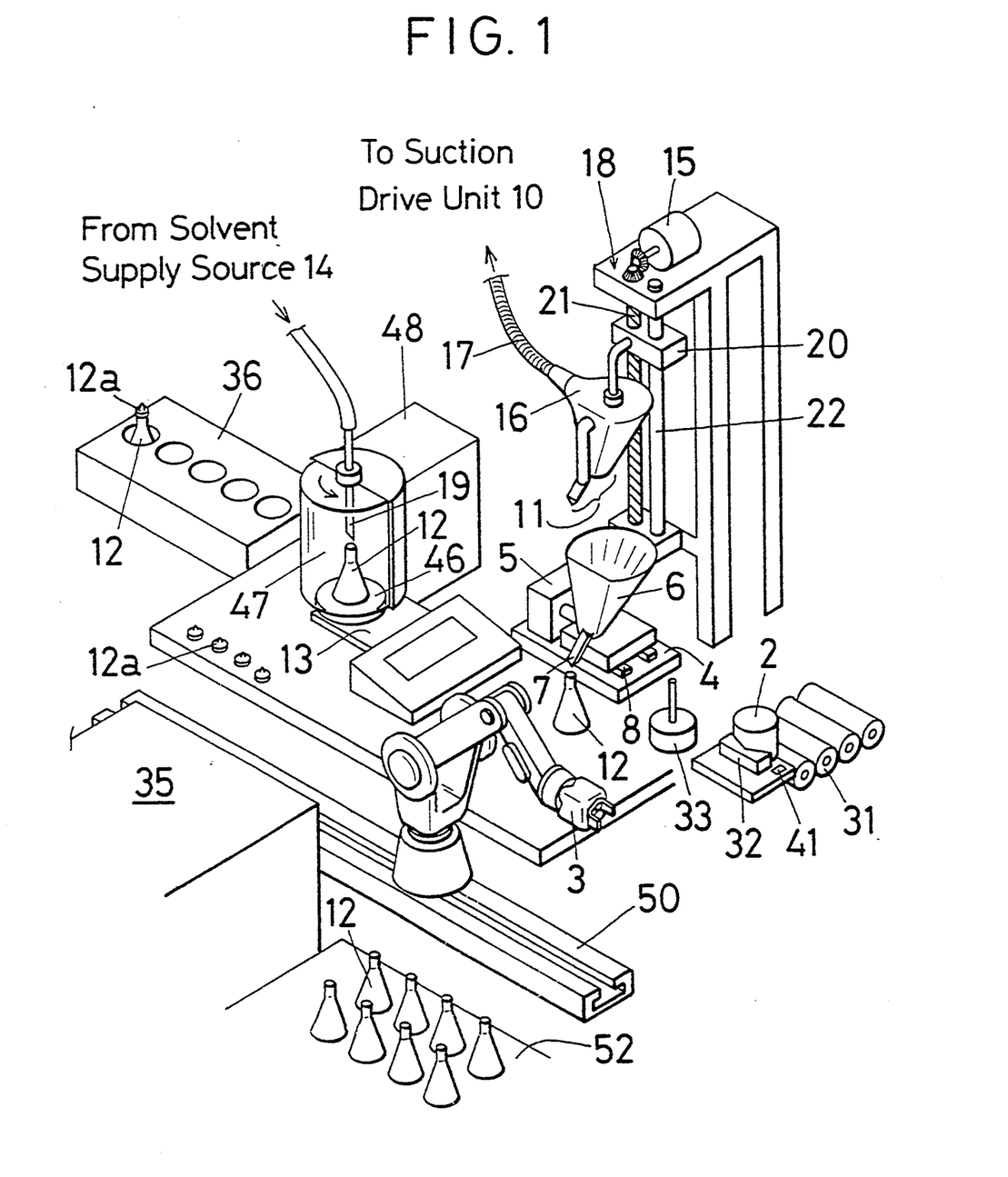
FIG. 1 is a perspective view illustrating an embodiment of the apparatus for automatically preparing a solution of a powdery product as a specimen for use in viscosity-determination according to the present invention.

FIG. 1 is a perspective view of an embodiment of the apparatus for automatically preparing a solution of a powdery product as a specimen for use in the viscosity measurement according to the present invention.

As seen from FIG. 1, hopper 6 and vibration drive unit 5 connected to hopper 6 are mounted on electronic discharge-weighing device 4 through shock absorber 8. Vibration-generating drive unit 5 is an electromagnetic vibrator. V-shaped discharge chute 7 is communicated to the lower opening of hopper 6. Discharge chute 7 is downwardly inclined to such an extent that a powdery sample contained in hopper 6 flows down the chute when vibrator 5 starts vibrational motion, but does not cause free flow or is free from gravitational flow when vibrator 5 is at rest. Dissolution container 12 is placed just below the tip of discharge chute 7 so as to receive the powdery sample discharged from hopper 6. Dissolution container 12 is an Erlenmeyer flask of stainless steel. Shock absorber 8 is a cushion made of a rubber and serves to prevent any transmission of the vibrational motion of vibrator 5 to electronic discharge-weighing device 4.

Suction port 11 is positioned on electronic dicharge-weighing device 4 in such a manner that the port can move up and down. Suction port 11 is connected to suction drive unit 10 through suction box 16 and hose 17 and an opening at the tip thereof has a shape which is in agreement with those of the bottom of hopper 6 and the bottom of V-shaped discharge chute 7. In addition, a plurality of openings are formed on the side wall of suction box 16 in order to suck the powdery sample adhered to the side wall of hopper 6 therein. The distance between these openings and the side wall and bottom of hopper 6 or between the openings and the bottom of discharge chute 7 preferably ranges from about 0.5 to 5 mm. Suction box 16 is fitted to female screw box 20, female screw box 20 is screwed in screw bar 21 which is connected to a motor serving as drive unit 15 for advancing and retreating (or moving up and down) screw box through bevel gear 18 and screw box 20 moves up and down along guide bar 22 so that suction port 11 can move down to the position in close proximity to the bottom of hopper 6 and that of discharge chute 7. In this respect, this upward and downward movement may be performed through the use of an air cylinder or an oil hydraulic cylinder as a drive unit. Drive unit 15 can rotate in such a manner that the ascending speed of suction port 11 is controlled to the range of from 5 to 40 cm/sec. If the powdery sample is adhered to the side wall of hopper 6, the suction port 11 ascends and simultaneously sucks the powdery sample adhered to the side wall while motor 15 controls the ascending speed of suction port 11 in the manner discussed above. Therefore, suction port 11 is not pressed against the side wall of hopper 6 through the powdery sample and accordingly electronic discharge-weighing device 4 on which hopper 6 is mounted is not damaged at all.

The apparatus comprises roller conveyor 31 for transporting sample container 2 accommodating the powdery sample and stopper 32 for fixing which are arranged in the vicinity of electronic discharge-weighing device 4. Sample container 2 accommodates approximately all of the powdery sample required for preparing a series of solutions and discharged from electronic discharge-weighing device 4. Container sensor 41 is positioned on the side face of roller conveyor 31. Stirring means 33 is arranged in the proximity to stopper 32 for fixing, the stirring means being equipped with a needle-like part having a length slightly greater than the depth of sample container 2.

Roller conveyor 31 is connected, as shown in FIG. 2, to tunnel furnace 24 which comprises heating-drying zone 24a, buffer zone 24b and ordinary temperature zone 24c. Heating-drying zone 24a maintains the internal atmosphere at a predetermined temperature through the action of infrared heater 25 under the control of a feedback type PID. Shutter 28 is positioned between heating-drying zone 24a and buffer zone 24b so that buffer zone 24b is communicated to or isolated from zone 24a and that the air from ordinary temperature zone 24c does not flow into zone 24a. The outside air is introduced into ordinary temperature zone 24c through the operation of fan 27. Conveyor 26 runs through tunnel furnace 24 and roller conveyor 31 is in contact with conveyor 26. For this reason, if sample container 2 accommodating the powdery sample is put on conveyor 26, the powdery sample is in order heated, dried and cooled down to the temperature of the outside air while passing through tunnel furnace 24 and finally transferred to roller conveyor 31.

Electronic balance 13 is arranged on the side of electronic discharge-weighing device 4 opposite to the side on which conveyor 31 is positioned. Weighing table 46 of electronic balance 13 can be covered with hood 47 for protecting the balance from the wind during weighing, hood 47 being opened and closed by the operation of drive unit 48. Nozzle 19 for injecting a solvent is arranged in such a manner that it passes through hood 47 and is directed toward the center of weighing table 46 of electronic balance 13. Solvent-injection nozzle 19 is connected to solvent supply source 14 (not shown in FIG. 1, see FIG. 3). In solvent supply source 14, a solvent, nitrobenzene is used as a solvent in this embodiment, is pumped up from a tank for storing solvent by a pump and supplied to dissolution container 12. An electromagnetically operating valve is arranged in the middle of the supply system to control the solvent supply. This device for solvent supply may be an electronic burette.

Moreover, heating-stirring device 36 is positioned in the vicinity of electronic balance 13. Heating-stirring device 36 is provided with 5 holes, corresponding to the number of specimens required for viscosity-determination of each powdery sample, so as to hold dissolution containers 12. Device 36 is equipped with a heating plate at the bottom thereof and a control means is attached thereto to maintain the temperature thereof at a constant level. A motor for operating a magnetic stirrer is embedded in the bottom portion thereof.

Guide rail 50 is arranged along conveyor 31, electronic discharge-weighing device 4, electronic balance 13 and heating-stirring device 36, and robot 3 is mounted on guide rail 50 so that robot 3 can automatically move along guide rail 50.

Viscosity-determining device 35 is positioned on the side of guide rail 50 opposite to the side on which the foregoing elements are arranged and within the range in which robot 3 can move or perform its operations. Viscosity-determining device 35 usable herein may be an automatic viscosity-determining device available from Rigo Co., Ltd. under the trade name of VSM-052PC.F01.

Figure 3:
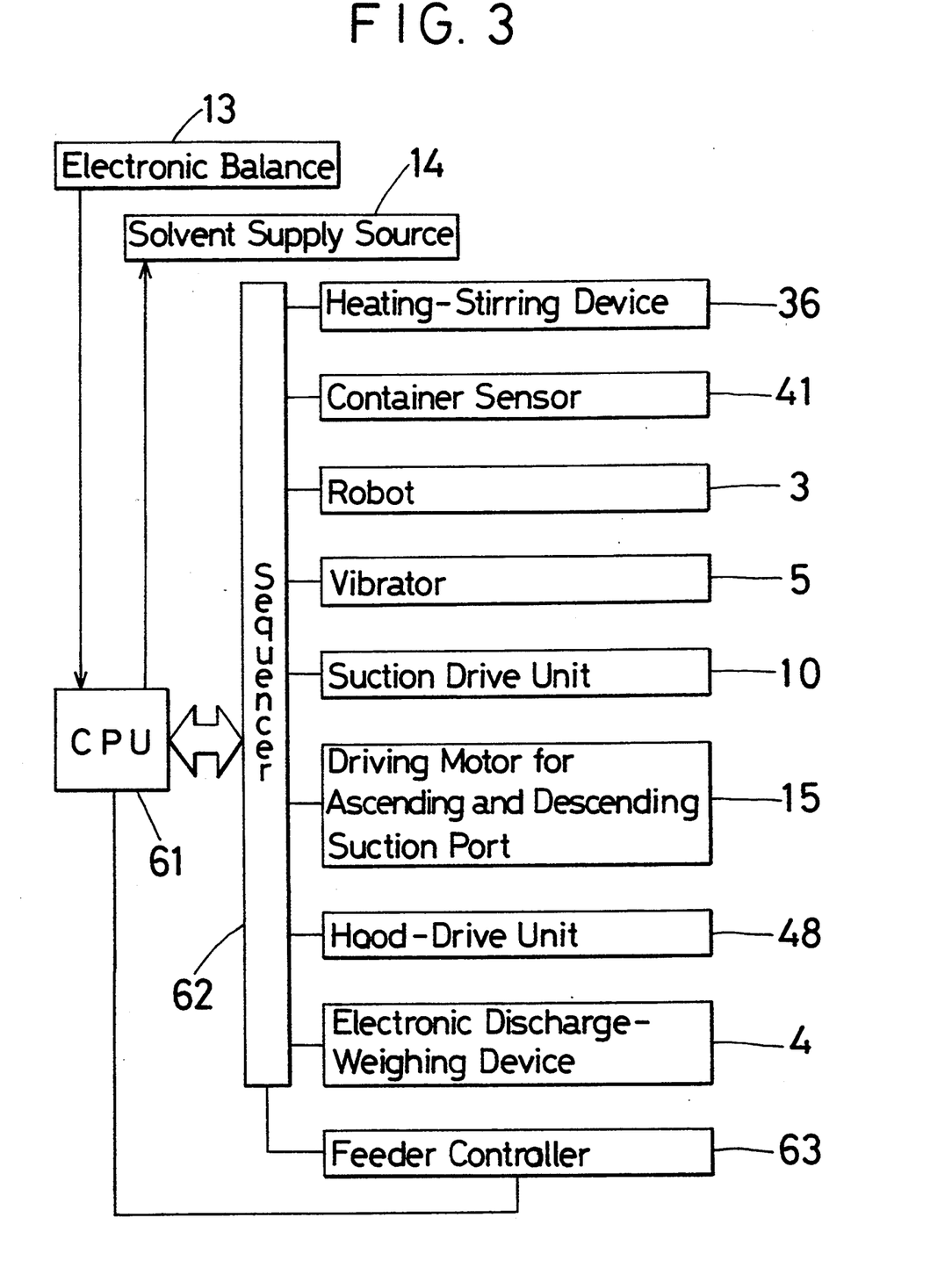
FIG. 3 is a block diagram illustrating the control system for the apparatus for automatically preparing a solution of a powdery product as a specimen for use in viscosity-determination according to the present invention.

In the foregoing apparatus, heating-stirring device 36, container sensor 41, robot 3, vibrator 5, suction drive unit 10, driving motor 15 for moving the suction port up and down and drive unit 48 for moving the hood of electronic balance 13 are, as shown in FIG. 3, connected to sequencer 62 and sequencer 62 is in turn connected to arithmetic and control unit 61 (central processing unit: CPU). Furthermore, electronic balance 13 and solvent supply source 14 are connected to arithmetic and control unit 61. Electronic discharge-weighing device 4 is connected to arithmetic and control unit 61 and sequencer 62 through feeder-controller circuit 63.

The apparatus for automatically preparing a solution of a powdery product as a specimen for viscosity-determination according to the present invention is in general operated in the following manner. The overall control of the apparatus is performed in accordance with the program incorporated into CPU 61 while the function of each individual device is controlled according to the control programs incorporated into sequencer 62. The function of the apparatus will hereunder be detailed in the light of the program chart incorporated into CPU 61 shown in FIG. 4 and the control program chart incorporated into sequencer 62 depicted as a subroutine A (see FIG. 5) and a subroutine B (see FIG. 6) for the program chart of the CPU 61.

The powdery sample is dispensed into sample container 2 in an amount roughly equal to that required for the preparation of specimens used in viscosity-determination of the powdery sample in the viscosity-determining device 35 and put on conveyor 31. The powdery sample is transferred to tunnel furnace 24 and it is in order heated, dried and cooled down to the temperature of the outside air in the course of the passage of sample container 2 through tunnel furnace 24.

Figure 4:
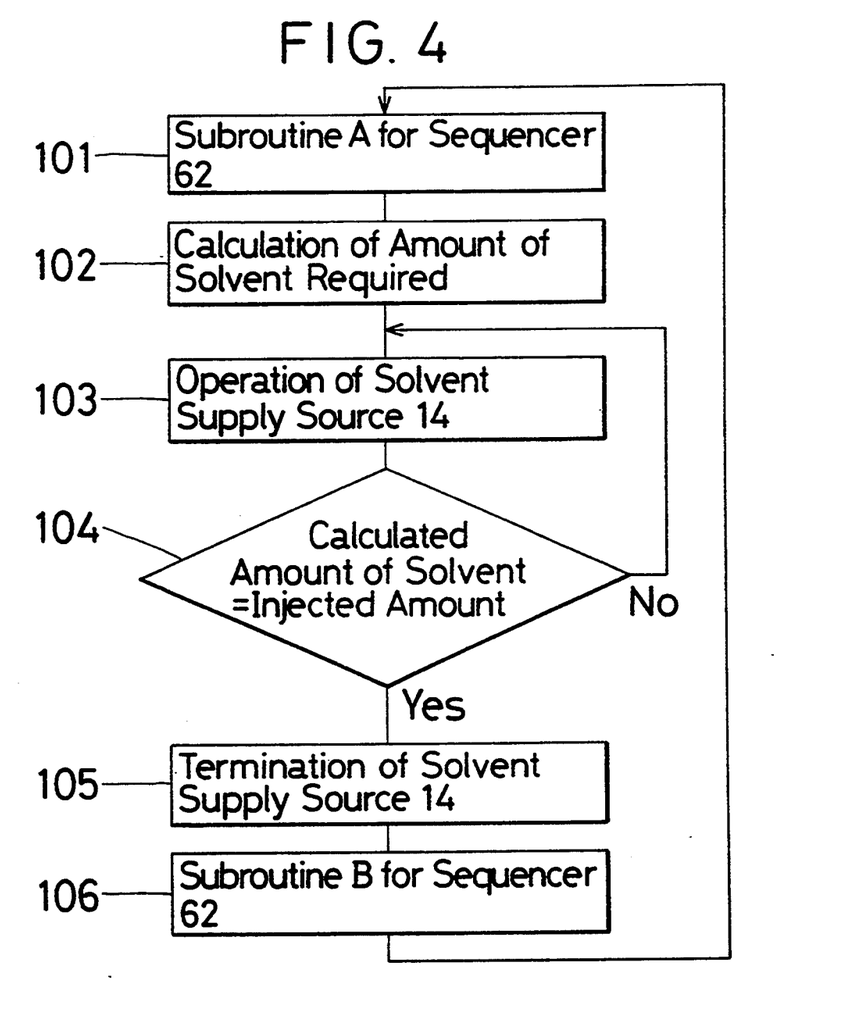
FIG. 4 is a program chart for an arithmetic and control unit used in the apparatus according to the present invention.

In step 101 shown in FIG. 4, sequencer 62 executes the operation of the subroutine A according to the Instruction outputted from CPU 61.

Figure 5:
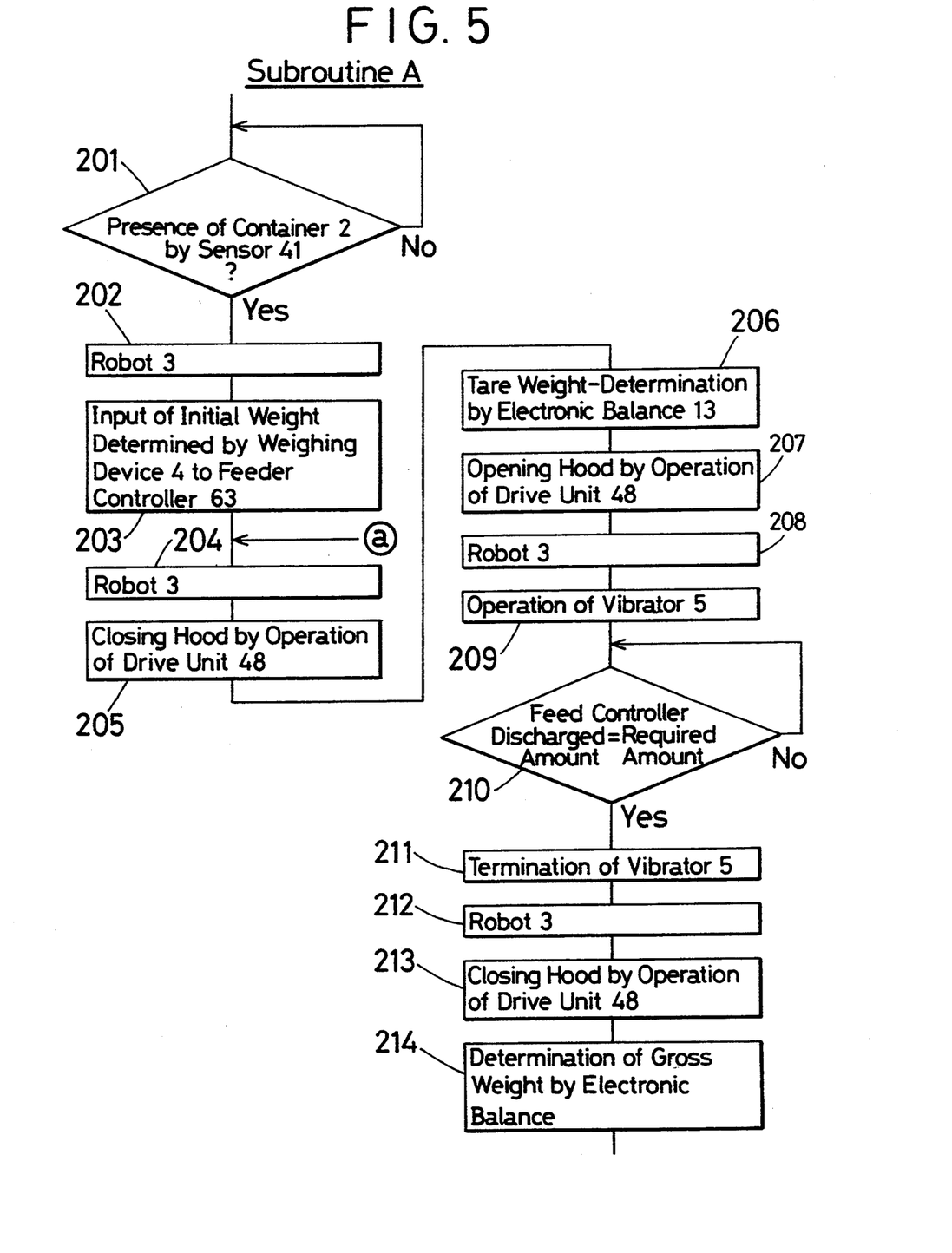
FIG. 5 is a program chart for controlling a sequencer used in the apparatus of the present invention.

After container sensor 41 detects the presence of sample container 2 which strikes against stopper 32 for fixing and is thus stopped, in step 201 shown in FIG. 5 (subroutine A), robot 3 is operated as follows in step 202. Robot 3 holds stirring means 33, turns the means upside down. Stirring means 33 downwardly inserts its needle-like part into sample container 2 and stirs the sample to finely pulverize it since it has which is formed into clusters through the foregoing heating and drying operation. Thereafter, the needle-like part of stirring means 33 is directed upward, inserted into suction port 11 to remove the resin powder adhered to the needle-like part by operating suction drive unit 10 and stirring means 33 is returned to its original position. Further robot 3 holds and lifts up sample container 2 to transfer it to a position above hopper 6, sample container 2 is then turned upside down through the rotation of the tip of robot 3 and thus the powdery sample is dropped to and stored in hopper 6. At this stage, electronic discharge-weighing device 4 determines the initial weight of the powdery sample and outputs the result to feeder controller circuit 63 wherein the initial weight thereof is stored (step 203).

In step 204, robot 3 serves to hold dissolution container 12 placed on table 52 and to put it on weighing table 46 of electronic balance 13 whose hood 47 is opened. A magnet as a stirrer tip is introduced into dissolution container 12 in advance. After starting drive unit 48 to close hood 47 (step 205), electronic balance 13 executes its weighing operation and stores the resulting weighed value, i.e., the tare weight of dissolution container 12 and the magnetic stirrer tip (step 206). After drive unit 48 is inversely operated to open hood 47 (step 207), dissolution container 12 is withdrawn from weighing table 46 and put on a position immediately below the tip of discharge chute 7 of discharge-weighing device 4 through the action of robot 3 (step 208).

When vibrator 5 is then put in operation in step 209, the powdery sample is discharged from hopper 6. Vibrator 5 is terminated (step 211) at an instance when the amount of the powdery sample outputted from discharge-weighing device 4 reaches the level required for the preparation of a specimen (step 210). Robot 3 is again operated (step 212) such that dissolution container 12 containing the desired amount of the powdery sample is put on weighing table 46. Then hood 47 is closed by the operation of drive unit 48 (step 213), subsequently electronic balance 13 determines the total gross weight of dissolution container 12 (inclusive of the tare weight of container 12; in step 214) and forwards the difference between the gross weight and the tare weight stored in the foregoing step 206, i.e., the net weight of the powdery sample to CPU 61 through feeder controller circuit 63.

Then the weight of the solvent required for the preparation of a specimen is calculated, in step 102 shown in FIG. 4, on the basis of the net weight of the powdery sample inputted to arithmetic and control unit 61 through the subroutine A as has been explained above. In this respect, it is defined by JIS-K-6721 that the concentration control of a solution should be performed on the basis of the volume of the solution, but the apparatus according to the present invention is designed such that the concentration control can be performed on the weight-basis while calculating the weight of the solvent required using the specific gravity thereof. In step 103, solvent supply source 14 is put in operation through the control of arithmetic and control unit 61 and thus the calculated amount of the solvent is injected, through solvent-injection nozzle 19, into dissolution container 12 which is placed on weighing table 46 and accommodates the desired amount of the powdery sample. The weight of the solvent injected into container 12 is determined by electronic balance 13. After the injection of the desired amount of the solvent (step 104), solvent supply source 14 is interrupted (step 105).

In the next step 106, sequencer 62 executes the operation of the subroutine B. In step 301 of the subroutine B shown in FIG. 6, hood 47 is opened through the operation of hood-drive unit 48 and then (in step 302) robot 3 holds and lifts up dissolution container 12 containing the required amounts of the powdery sample and the solvent placed on weighing table 46, then transfers container 12 to the specified hole of heating-stirring device 36 and dissolution container 12 is covered with cap 12a. At this stage, hopper 6 and discharge chute 7 are cleaned to remove the powdery sample remaining thereon. When driving motor 15 for moving suction port 11 up and down is operated in step 303, suction port 11 descends toward the position in close proximity to the bottom portions of hopper 6 and discharge chute 7. When suction-drive unit 10 is put in operation (step 304), the powdery sample remaining on hopper 6 and discharge chute 7 is sucked therein through suction port 11, suction box 16 and hose 17. After the completion of the sucking operation, driving motor 15 for moving suction port 11 up and down is inversely rotated to ascend and return suction port 11 to its original position (step 305).

Figure 6:
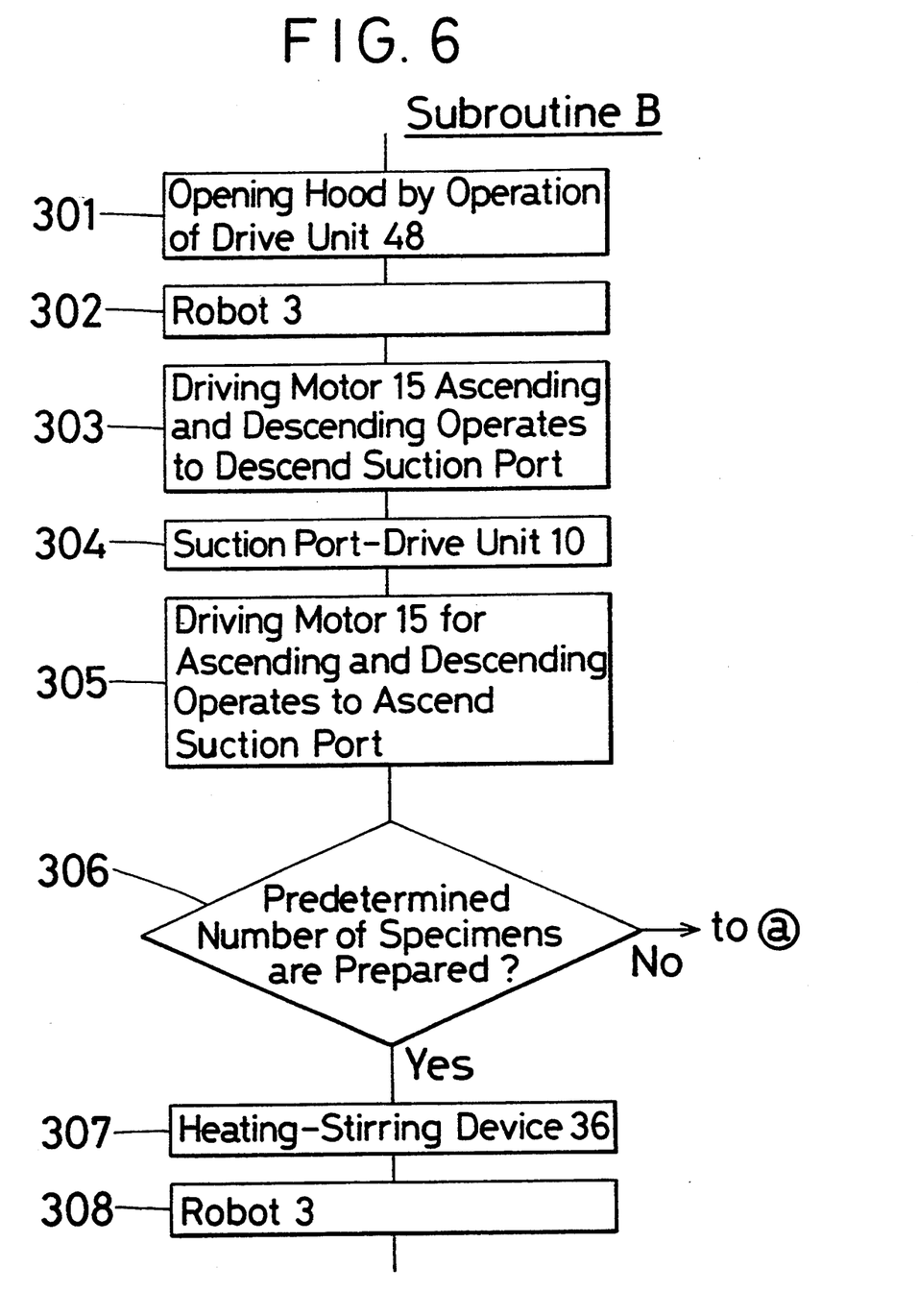
FIG. 6 is a program chart for controlling a sequencer used in the apparatus of the present invention.

On the other hand, the number of dissolution containers 12 which have been transferred, in the foregoing step 302, to heating-stirring device 36 is confirmed or detected (step 306). If a desired number of specimens, i.e., dissolution containers 12 have not yet been prepared, the operation should be returned to the step 204 for the subroutine A and the operations subsequent to this step should be repeated over a desired number of times. After a desired number of specimens are prepared, the motor of the stirrer which is a constituent of heating-stirring device 36 is put in operation (step 307), the magnetic stirrer tip contained in dissolution container 12 is correspondingly rotated and thus agitates the powdery sample and the solvent to thus dissolve the powdery sample in the solvent. It takes a certain time to completely dissolve the sample in the solvent. In this respect, the heating plate of heating-stirring device 36 is heated to a temperature of 105° C. in advance. In this way, a specimen having a predetermined concentration is prepared. Then robot 3 removes, in order, caps 12a from dissolution containers 12 containing specimens, takes out the containers from heating-stirring device 36 and transfers them to viscosity-determining device 35 (step 308). Incidentally, it is confirmed in the step 306 whether a predetermined number of dissolution containers 12 are provided or not. However, if a subsequent sample is not detected over a predetermined time, the dissolution operation is terminated even if a predetermined number of dissolution containers 12 are not provided and dissolution containers 12 containing specimens are transferred to viscosity-determining device 35 in order to prevent the reduction in the operating efficiency of the apparatus due to any retardation of sample transportation.

As has been discussed above in detail, the apparatus for automatically preparing a solution of a powdery product as a specimen for use in viscosity-determination according to the present invention does not require much labor and time. The concentration of the solution thus prepared does not vary depending on the operators. Thus, the apparatus of the present invention ensures high reproducibility of the viscosity measurement and this in turn improves the accuracy of the average degree of polymerization calculated on the basis of the viscosity-determination.

What is claimed is:

1. An apparatus for preparing a solution of a powdery product having a predetermined concentration as a specimen for use in viscosity measurement, said apparatus comprising an electronic discharge-weighing device for determining the discharged amount of a powdery sample which is accommodated in a sample container, introduced into a hopper and discharged from the hopper by a vibration-generating drive unit; a dissolution container for receiving and dissolving the powdery sample from the hopper; an electronic balance for weighing the powdery sample in the dissolution container; a solvent supply source for injecting a solvent into the dissolution container containing the powdery sample; a device for heating and stirring the powdery sample and the solvent in the dissolution container; and a control circuit for controlling the electronic discharge-weighing device, the vibration-generating drive unit, the electronic balance, the solvent supply source and the heating and stirring device.

2. The apparatus of claim 1, further comprising a robot for holding and transferring the sample container during and between the sample weighing and hopper introducing operations, said dissolution container and the robot being controlled by the control circuit.

3. The apparatus of claim 2, further comprising a viscosity-determining device within the active region of the robot.

4. The apparatus of claim 1, further comprising a tunnel furnace for drying the powdery sample therethrough with a conveyor, on the side from which the powdery sample is supplied, having a heating-drying zone circulating hot air by an infrared heater, a buffer zone for maintaining the temperature in the heating-drying zone at a predetermined level, and an ordinary temperature zone circulating outside air.

5. The apparatus of claim 1, further comprising a discharge chute connected to a lower opening of the hopper and inclined to such an extent that the powdery sample is free from gravitational flow and flows down the chute only by the vibrational motion applied thereto through the vibration-generating drive unit, which is operated based on a weighed value by the control circuit inputted from the electronic discharge-weighing device which device has also previously adjusted the weight of the powdery sample discharged from the hopper.

6. The apparatus of claim 1, wherein the hopper connected to the vibration-generating drive unit is mounted on the electronic discharge-weighing device through a shock absorber.

7. The apparatus of claim 1, further comprising a suction port in communication with a suction drive unit and fixed to a driving device for moving the suction port up and down to a position in close proximity to the bottoms of the hopper and the discharge chute.

8. The apparatus of claim 7, wherein the suction port is formed into a box body having a shape approximately similar to shapes of the hopper and the discharge chute and is positioned to maintain in close proximity to the side walls and the bottoms of the hopper and the discharge chute.

9. The apparatus of claim 7, wherein ascending speeds of the suction port to the hopper and the discharge chute are controlled to be not more than 40 cm/sec by the driving device.

10. The apparatus of claim 7, wherein the suction port is positioned to maintain a distance ranging from 0.5 to 5 mm to the side walls and the bottoms of the hopper and the discharge chute.

11. The apparatus of claim 1, wherein the powdery product is vinyl chloride resin powder.

12. The apparatus of claim 8, wherein ascending speeds of the suction portion to the hopper and the discharge chute are controlled to be not more than 40 cm/sec by the driving device.

13. The apparatus of claim 8, wherein the suction port is positioned to maintain a distance ranging from 0.5 to 5 mm to the side walls and the bottoms of the hopper and the discharge chute.

14. The apparatus of claim 9, wherein the suction port is positioned to maintain a distance ranging from 0.5 to 5 mm to the side walls and the bottoms of the hopper and the discharge chute.

* * * * *